United States Patent [19]

Pennington

[11] Patent Number: 5,186,621

[45] Date of Patent: Feb. 16, 1993

[54] CHIMNEY HOLDER AND INJECTION TUBE MOUNT FOR USE IN ATOMIC ABSORPTION AND PLASMA SPECTROSCOPY

[75] Inventor: H. Dale Pennington, Bryan, Tex.

[73] Assignee: The Texas A & M University System, College Station, Tex.

[21] Appl. No.: 734,194

[22] Filed: Jul. 22, 1991

Related U.S. Application Data

[63] Continuation-in-part of Ser. No. 500,367, Mar. 28, 1990, Pat. No. 5,033,850.

[51] Int. Cl.[5] .......................... F23D 14/62; G01J 3/30
[52] U.S. Cl. .................................... 431/354; 431/343; 431/154; 356/315
[58] Field of Search ............... 431/354, 343, 154, 355; 356/315; 285/139, 145, 423, 911

[56] References Cited

U.S. PATENT DOCUMENTS

| | | | |
|---|---|---|---|
| 2,517,666 | 8/1950 | Hood | 183/24 |
| 2,769,366 | 11/1956 | Honma | 88/14 |
| 2,990,748 | 7/1961 | Vallee et al. | 431/354 |
| 3,267,699 | 8/1966 | Kniseley | 431/355 X |
| 3,469,789 | 9/1969 | Simmons | 239/338 |
| 3,516,771 | 6/1970 | Redina | 431/126 |
| 3,525,476 | 8/1970 | Boling et al. | 239/338 |
| 3,592,608 | 7/1971 | White | 23/253 |
| 3,806,250 | 4/1974 | George | 356/87 |
| 4,125,225 | 11/1978 | Venghiattis | 239/338 |
| 4,220,413 | 9/1980 | Targowski et al. | 356/315 |
| 4,367,042 | 1/1983 | Smith, Jr. et al. | 356/315 |
| 4,568,267 | 2/1986 | Kendall-Tobias | 431/90 |
| 4,624,565 | 11/1986 | Kiminkinen | 356/315 |
| 4,678,428 | 7/1987 | Tanaka et al. | 431/355 X |
| 4,688,722 | 8/1987 | Dellassio et al. | 239/81 |
| 4,766,287 | 8/1988 | Morrisroe | 219/121.52 |
| 4,803,051 | 2/1989 | Knapp | 422/80 |

OTHER PUBLICATIONS

*Atomic Spectroscopy Supplies Catalog*, pp. 22, 23 (Spring, 1991).

Advertisement for Prealigned Sample Introductory Assembly as manufactured by Leemans, Perkin Elmer and others.

*Primary Examiner*—Larry Jones
*Attorney, Agent, or Firm*—Arnold, White & Durkee

[57] ABSTRACT

A modified quartz element having plasma and auxiliary gas ports, a upper chimney mount, a unique chimney holder and injection tube mount, and a compression plug is disclosed. The chimney holder and injection tube mount includes a specially machined groove so that a unique, double O-ring seal between the mount and the quartz element may be developed. The injection tube mount also includes a specially designed bore for receiving two O-rings so that the injector tube is supported in and sealed with the mount only through the use of resilient O-rings.

31 Claims, 9 Drawing Sheets

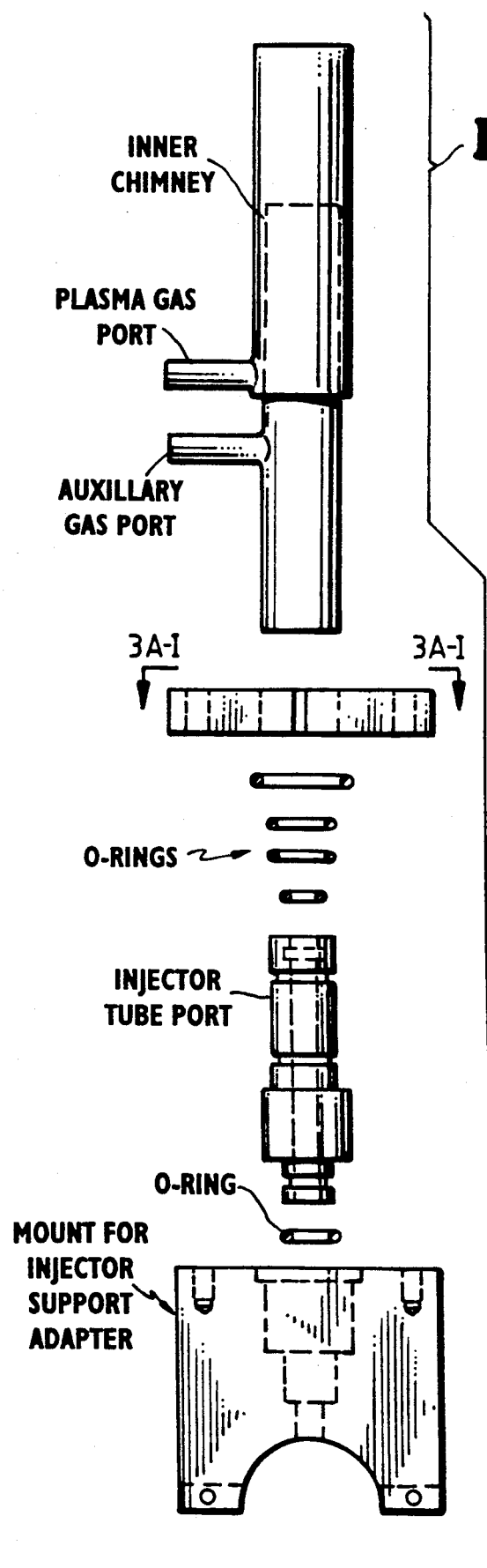
Fig. 3 A-I
(PRIOR ART)
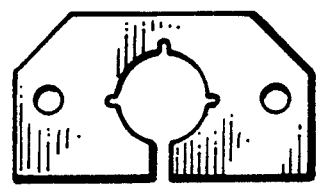
Fig. 3 A-II
(PRIOR ART)
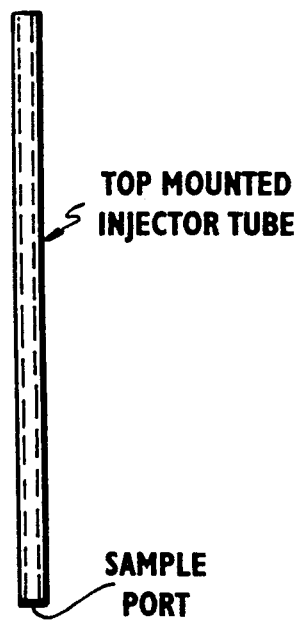
Fig. 3 B
(PRIOR ART)

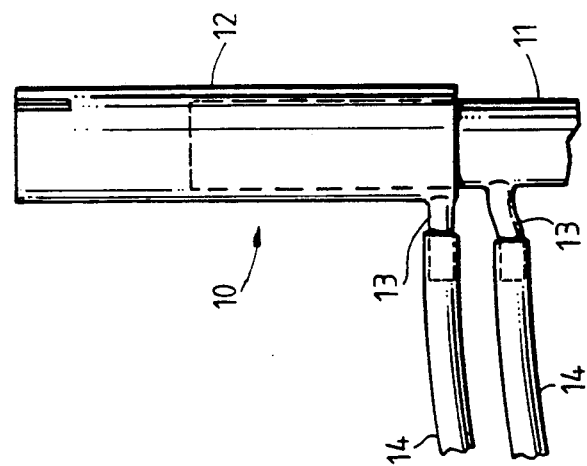
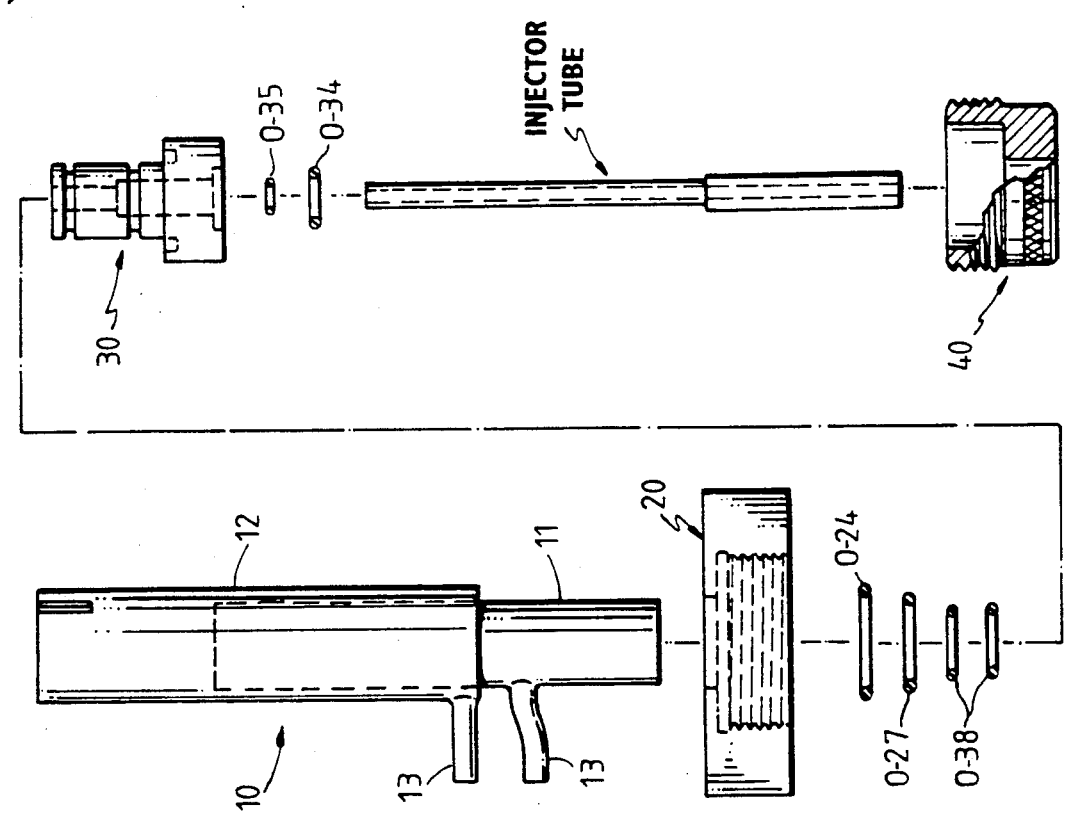

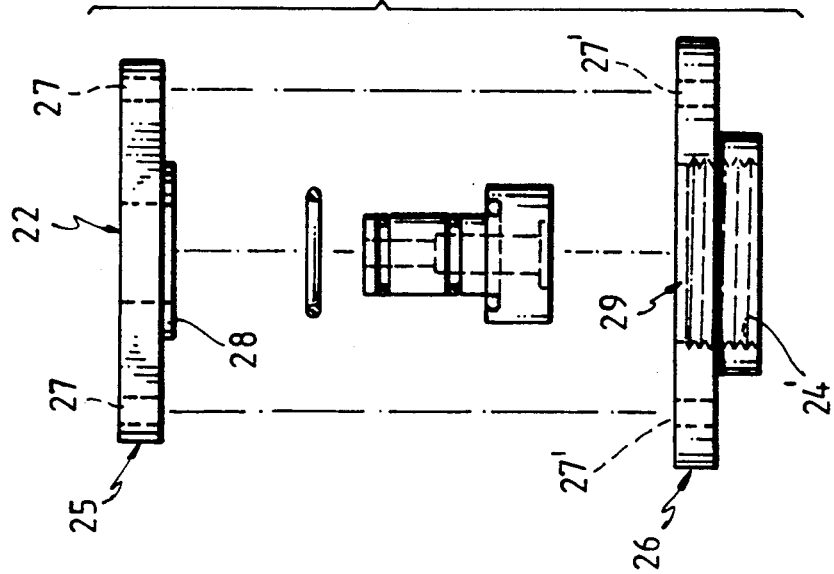
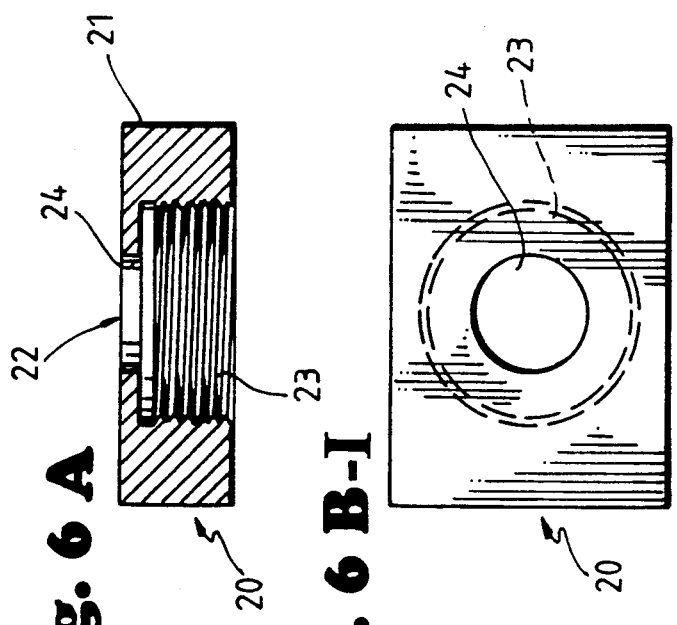
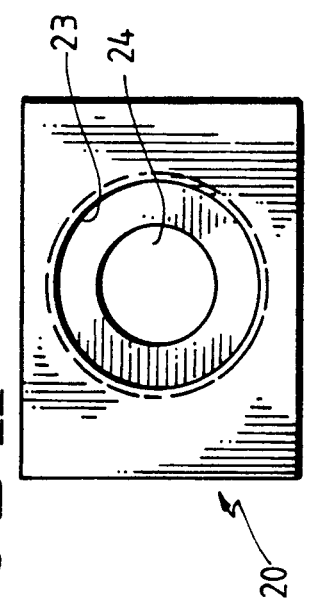

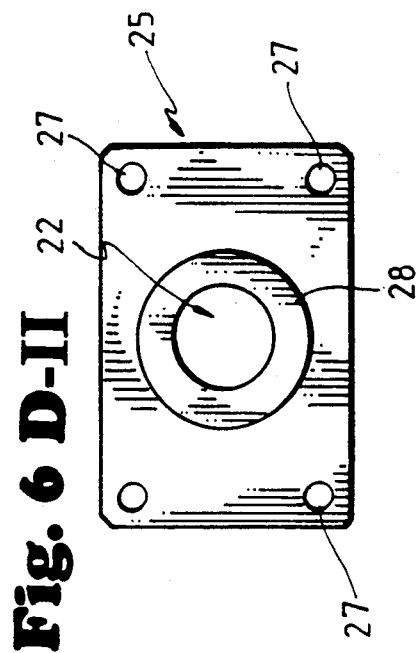
Fig. 6 D-II
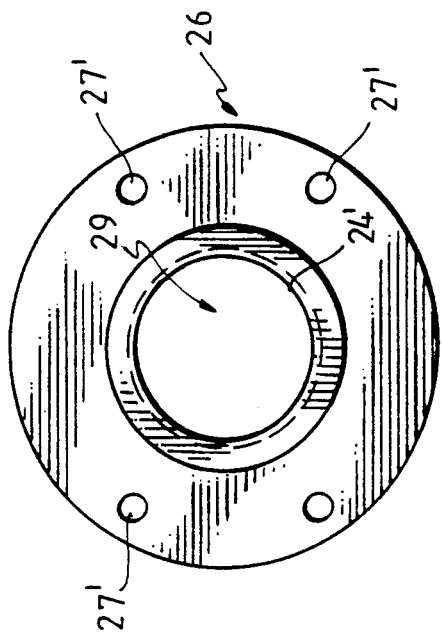
Fig. 6 D-IV
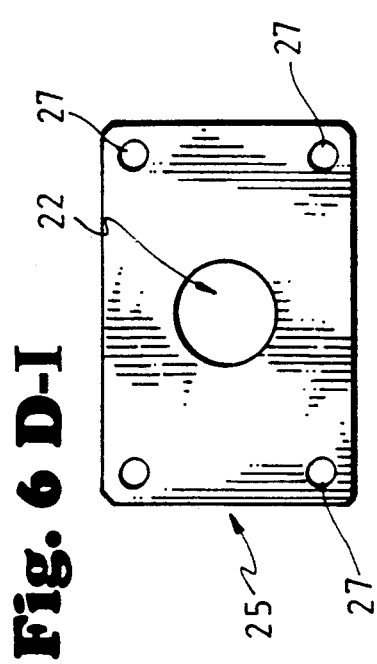
Fig. 6 D-I
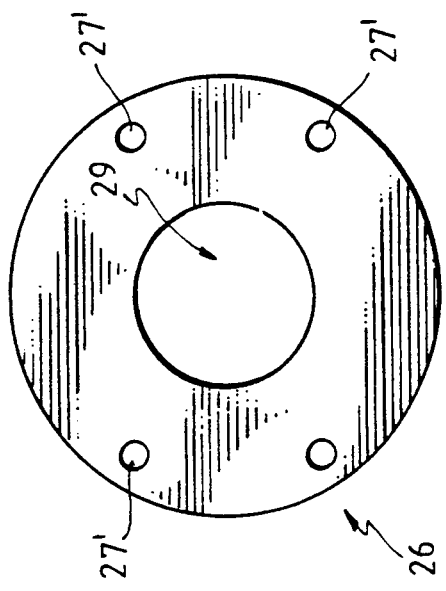
Fig. 6 D-III

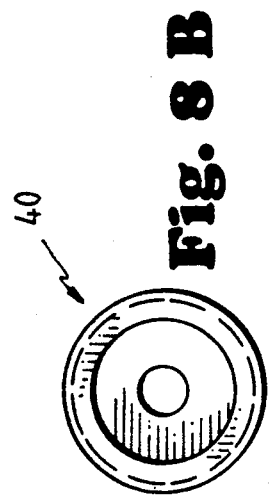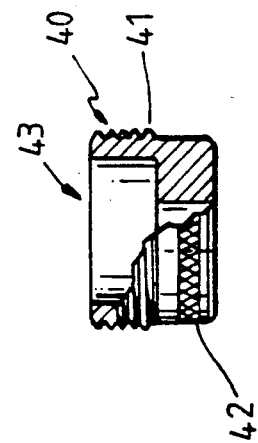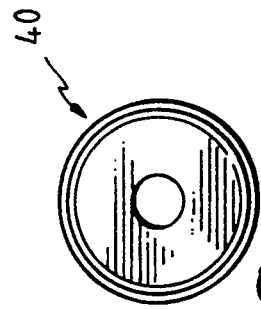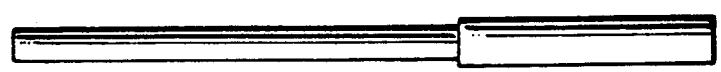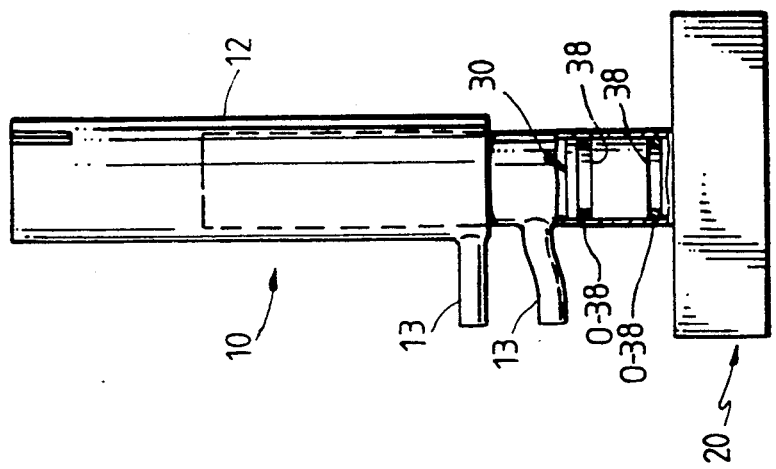

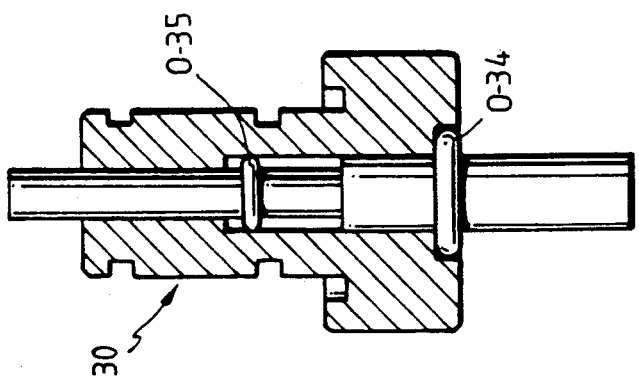
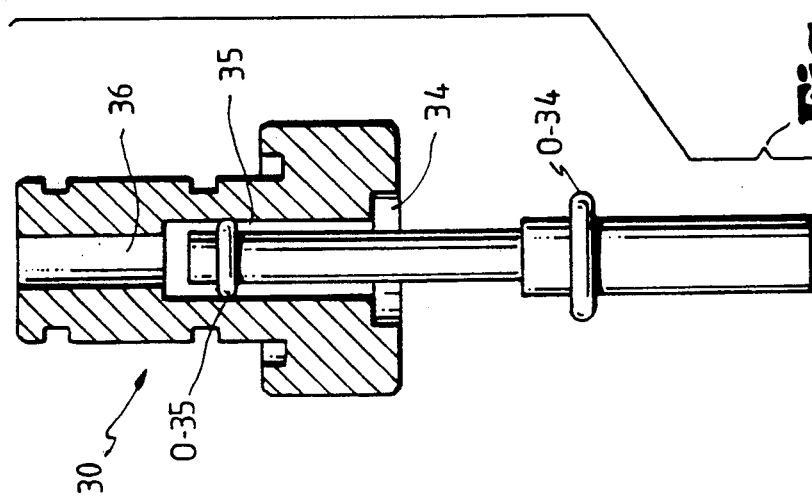
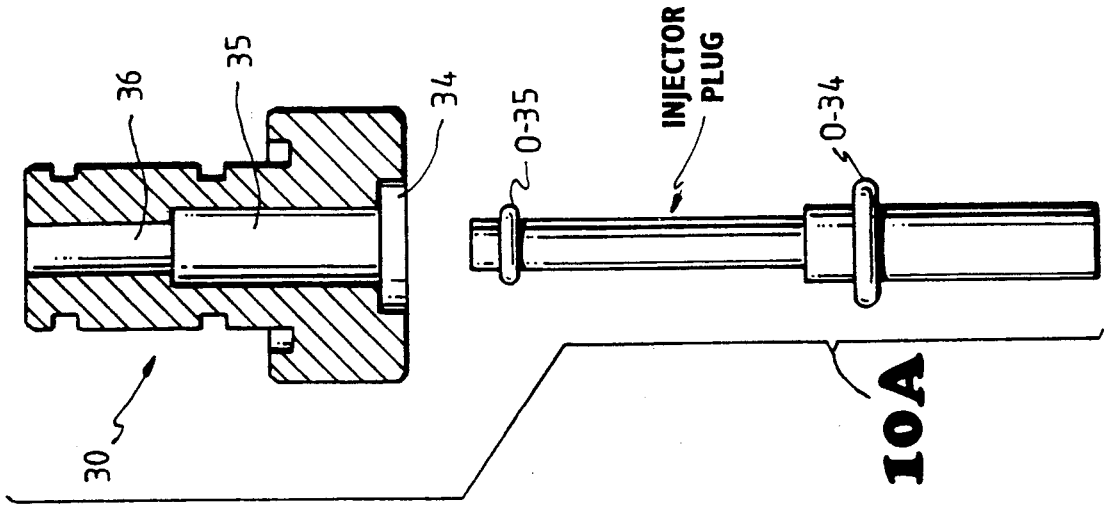

CHIMNEY HOLDER AND INJECTION TUBE MOUNT FOR USE IN ATOMIC ABSORPTION AND PLASMA SPECTROSCOPY

CROSS REFERENCE TO RELATED APPLICATIONS

This application is a continuation-in-part of co-pending application Ser. No. 500,367 entitled GAS FLOW CHAMBER FOR USE IN ATOMIC ABSORPTION AND PLASMA SPECTROSCOPY filed on Mar. 28, 1990 by H. Dale Pennington now U.S. Pat. No. 5,033,850.

1. BACKGROUND OF THE INVENTION

1.1 Field Of The Invention

The present invention pertains generally to atomic absorption and plasma spectrometers, and more particularly, to spectroanalytical systems of the type that sense a special characteristic of a flame by absorption or emission technology. The present invention more specifically pertains to an assembly for reducing the amount of leakage in a plasma torch.

1.2 Description of the Prior Art

In atomic absorption and plasma spectroscopy, measurement of the absorption or emission of radiation at a characteristic resonant spectral line for a particular element yields a measure of the concentration of that element in an original sample. Presently, the most common technique for atomizing an element for purposes of absorption measurement is by introducing a liquid sample containing the element of interest into a gas burner wherein droplets of the sample are vaporized and the elements ultimately atomized so as to form a radiation beam. In plasma emission systems, for example in an inductively coupled plasma (ICP) spectrometer, a liquid sample is nebulized with a plasma gas such as argon, nitrogen, etc. The sample liquid is suspended in micro-sized droplets which are introduced into the plasma torch wherein the atoms of the liquid are energized from the plasma. Energy emitted by the energized sample is measured by the spectroanalytical system.

In atomic absorption or emission type spectroanalytical systems, the material to be analyzed is introduced into a premix or gas flow chamber by a nebulizing arrangement using a regulated plasma gas or oxidant stream. The plasma gas or oxidant stream is ideally introduced into the gas flow chamber as a fine uniform spray of minute droplets, which droplets are entrained with a combustible fuel or plasma gas and flow through the gas flow chamber into a burner or plasma torch. Upon combustion, the combustible fuel energizes the material to be analyzed for purposes of analysis. In plasma units, the plasma torch energizes the material. An example of a nebulizer arrangement is seen in U.S. Pat. No. 4,220,413.

In ICP systems, the liquid sample is introduced into a plasma torch having a quartz chimney through a specially designed injection tube. Generally, a single assembly serves as both a support (or holder) for the quartz chimney and a mount for the injection tube. This assembly is generally referred to herein as the torch support assembly.

Because of the extreme heat associated with ICP systems, it is important to allow for the heat expansion of the quartz chimney, the injector tube, and their supporting apparatus. Absent such allowance, the quartz chimney and its supporting apparatus are prone to break when subjected to extreme temperatures. This is undesirable both because of the expense in labor and parts of repairing or replacing the broken parts and the opportunity costs lost when the ICP system is down. Additionally, because quartz chimneys are relatively fragile, frequent repair or replacement of torch support assemblies usually results in breakage of several chimneys, which are often to expensive to replace. Thus, one desirable attribute for torch support assemblies is to provide for the heat expansion of the quartz chimney, the injector tube and their supporting apparatus.

Another desirable attribute of torch support assemblies is to inhibit the formation of leaks. Generally, when a leak occurs (i.e., when the plasma gas is exposed to air) arcing is likely to occur. Such arcing usually results in damage to the support assembly to such a degree that the support assembly must be replaced or repaired. As discussed above, this replacement or repair time is disadvantageous in terms of real costs, broken chimneys, and lost opportunity costs.

Given the importance of manufacturing and set-up costs it is also desirable that torch support assemblies be easily manufactured and assembled.

In an attempt to implement the desirable attributes discussed above, a number of prior art torch support assemblies have been developed. These assemblies may be divided into three basic groups: (1) those having non-segmented, blown quartz torch and chimney assemblies ("Quartz assemblies"); (2) those having segmented attachments for the quartz chimney, the plasma gas inlet, the auxiliary gas inlet, and the injection tube ("Type I assemblies"); and (3) those having two segmented attachments: one for the quartz chimney, the plasma gas inlet, and the auxiliary gas inlet; and another for the injection tube ("Type II assemblies").

1.2.1 Prior Art Quartz Assemblies

The Quartz assemblies generally comprise a unitary, non-segmented blown quartz element having a quartz injection tube, inlets for plasma and auxiliary gas, and a quartz chimney. One such torch support assembly is the Quartz Torch for ICP, PE No. 0047-2048, manufactured by Perkin-Elmer. An example of a Quartz assembly is illustrated in FIG. 1. In this type of assembly, the connection between the injection tube of the quartz element and the supply of the liquid spray sample is made through a ball and socket connector where one end of the unitary torch assembly, i.e., the ball, is brought into direct contact with a ball joint adaptor that is connected to the supply of the spray sample.

Since the quartz assemblies consist of a single, blown quartz element, they cannot accommodate alumina injection tubes. This is disadvantageous in that the melting or fusion point of an quartz injector tube is much less than that for an alumina one. As a result, when the injection tube of a quartz assembly becomes plugged or clogged it likely to melt or fuse together—destroying the integrity of the torch and requiring complete replacement of the quartz assembly.

Another disadavantage of quartz assemblies is that they are prone to leak if not precisely machined with very small tolerances. The unitary design of the quartz assemblies restricts the likely regions of gas leakage to the plasma and auxiliary gas ports and the ball joint and ball joint adaptor. Because the integrity of the seal at the ball joint depends an a close fit between the ball of the quartz assembly and the socket of the ball joint adaptor, it is essential that the quartz ball and the ball joint adaptor be machined to very precise tolerances. The requirement for such precise machining generally increases both the cost of Quartz assemblies and the likelihood that a particular assembly will leak.

1.2.2 Prior Art Type I Assemblies

In an attempt to overcome the shortcomings of quartz assemblies and to accommodate alumina injector tubes, Type I torch assemblies were developed. These assemblies generally comprise a quartz chimney, a upper tube guide including a plasma gas port and a chimney support, and a lower tube guide including an auxiliary gas port. Such assemblies accommodate alumina injector tubes which are supported by both the upper and lower tube supports. One Type I assembly is the Plasma II and Plasma 40 Type I Demountable Torch Assembly, PE No. 58-0161, manufactured by Perkin-Elmer. An example of a Type I assembly is provided in FIG. 2.

As illustrated in FIG. 2, Type I assemblies rely on three compressed O-rings to inhibit gas leakage—a first compressed O-ring to provide a seal between the outer portion of the quartz chimney and the upper tube guide; a second compressed O-ring to provide a seal between the upper and lower tube guides; and a third compressed O-ring to provide a seal between the injector tube and the tube port in the lower tube guide. The O-rings are compressed by placing a shield over the chimney/tube guide combination, affixing the shield to a base having a bore therethrough, and forcing a compression plug into the base. Because the seals in Type I assemblies rely on the compression of the three O-rings, it is often necessary to use a special tool to force the compression plug into the base.

There are several disadvantages associated with Type I assemblies, the most obvious being the extensive amount of parts. This large number of parts results in extended assembly time. Additionally, the many interfaces between these parts provide many regions where gas leakage can occur. As discussed above when the plasma or auxiliary gas leaks, i.e., makes contact with atmospheric air, the plasma is likely to arc to the site of the leak. Such an arc may carbonize that site resulting in either extinction of the plasma torch or analytical results that have a high coefficient of variation.

Another disadvantage of Type I assemblies are their reliance on O-ring compression for sealing. As noted above, a compression plug is forced into the base to urge the shield towards the upper tube guide, compressing the first O-ring; to urge the upper tube guide towards the lower tube guide, compressing the second O-ring; and to urge the injection tube towards the compression plug, compressing the third O-ring. Often the amount of pressure that must be applied by the compression plug is quite high. In fact, most prior art Type I assemblies require a special tool for affixing the compression plug to the base.

While tension on the compression plug results in compression of the O-rings, it also results in tension on the quartz chimney and the injector tube. Too much pressure on the chimney or the injector tube results in breakage. Because there is little indication (other than experience) that the compression plug is being improperly tightened, attempts to properly assemble a Type I assembly, or to fix a leak by tightening the compression plug, frequently result in breakage of either the quartz chimney, the injector tube, or both. Such breakage necessitates a disassembly of the torch and a replacement of the broken part.

Still another disadvantage of the Type I assembly is that it is inherently prone to O-ring failure. One inherent attribute of ICP torches is that they become extremely hot and give off extensive UV radiation during operation. As illustrated in FIG. 2, the first O-ring is situated in close proximity to the plasma gas flow and the region where the sample exits the injector tube. This location exposes the first O-ring to extensive heat and UV radiation given off by the torch at the point where the plasma gas and the sample spray combine. As a result of this exposure the sealing qualities of the O-ring are prone to degrade over time and cause leaks. Such leaks either require disassembly of the torch and replacement of the failed O-ring (with the repair costs and associated downtime) or a further tightening of the compression plug (with the risk of breaking the chimney or injector tube).

A still further disadvantage of the Type I assemblies is that they often provide inaccurate or erratic test results. As mentioned above, the Type I assemblies can accommodate alumina injector tubes. Thus, unlike Quartz assemblies, meltdown of the injector tube for Type I assemblies is uncommon. Type I assemblies, however, are often plagued by leakage due to seal failure at the bottom of the injector tube port. As illustrated in FIG. 2 a single O-ring is used to create a seal between the injector tube and the base. If this seal fails, inaccurate test results (due to non-uniformity in the sample flow) or plugging of the injector tube (eventually resulting in the extinction of the plasma) may occur. Since only a single O-ring is used to seal the injector tube, failure of that O-ring may destroy the integrity of the entire torch. Additionally, because the sealing potential of the O-ring rests on the amount of pressure applied by the compression plug, improper assembly of the torch (e.g, too little pressure on the compression plug) may result in improper operation.

A final disadvantage of the Type I assemblies is that is essentially impossible to adjust the height of the injector tube in relation to the quartz chimney. As illustrated in FIG. 2, the seal of the injector tube is effected by forcing the third O-ring against the base, while at the same time forcing the injector tube against a hard non-resilient lip of the bore in the base. Because support and sealing for the injector tube is obtained ony when the top of the large diameter portion of the injector tube is in contact with the lip, it is essentially inpossible to adjust the height of the injector tube. This inability to adjust the tube often results in less that optimal test results.

1.2.3 Prior Art Type II Assemblies

In addition to the Quartz and Type I assemblies, a third type of assembly, the Type II assembly exists in the prior art. Like the Quartz assemblies, and unlike the Type I assemblies, the Type II assemblies utilize a single blown quartz element that serves as the chimney and has ports for the plasma and auxiliary gas. Like the Type I assemblies, and unlike the Quartz assemblies, the Type II assemblies also have a separate, segmented attachment capable of accommodating alumina injector tubes. One example of a Type II assembly is the Type II Demountable torch, offered as part of a retrofit kit, PE No. 58-0538, manufactured by Perkin-Elmer. An example of a Type II assembly is illustrated in FIGS. 3A-I, 3A-II and 3B.

As illustrated in FIG. 3A-I and 3A-II, the Type II assembly comprises a quartz chimney having ports for plasma and auxiliary gas; an injector support adapter; a mount for the support adapter; and an upper torch clamp. The seal between the quartz chimney and the support adapter is obtained by applying coaxial pressure to the chimney by inwardly compressing the upper torch clamp and forcing the upper torch clamp towards the mount by inserting compression screws into threaded bores. The downward pressure generated by the upper clamp forces the base of the chimney against the upper O-ring, compressing the O-ring an producing a seal.

The injector tube for the Type II assemblies is slightly different than that used in the Quartz of Type I assemblies.; as illustrated in FIG. 3B. This tube is mounted in the Type II assemble by inserting it from the top (instead of the bottom as for the other prior art assemblies). A single O-ring inside the support adapter is responsible for establishing a proper seal.

The Type II assemblies suffer from many of the shortcomings associated with the other prior art assemblies. Initially, as with Type I assemblies, the integrity of the seal between the chimney and the support mount depends on the amount of pressure applied to an O-ring by the quartz chimney. As discussed above, this arrangement often results in improper seals or breakage of the chimney because too little or too much pressure is applied to the quartz chimney. Additionally, Type II assemblies utilize an slitted upper torch clamp that is secured by two screws. Because of the slit in the clamp and the use of only two screws, a non-uniform source of pressure is applied to the chimney, and thus to the sealing O-ring. Unless extreme care is taken in assembling this device, non-uniform pressure is applied to the O-ring resulting in auxiliary gas leaks.

A further problem with the Type II assemblies is the use of a single O-ring, positioned in the upper portion of the support adapter. As discussed above, the use of a single O-ring to seal the injector tube to the support mount necessitates disassembly of the entire torch whenever one O-ring fails. Further, for the Type II assembly, the injector tube O-ring is located proximate to the region where the sample stream exits the injector tube and where the plasma gas enters the torch. Again, exposure to the UV radiation and heat generated in this region tends to degrade the O-ring. Past experience with Type II assemblies indicates leaks generally occur after one to two weeks of use due to heat and UV degradation of the injector tube O-ring.

2. SUMMARY OF THE INVENTION

The present invention addresses the aforementioned and other disadvantages of prior art torch support assemblies by providing an improved assembly compatible with conventional spectroanalytical apparatus. Use of the present system results in improved test results, i.e., a constant coefficient of variation for three replications below 2% each day, while significantly reducing the amount of time required for assembly and repair. In contrast to the prior art assemblies where repair or replacement is often required on an hourly or a weekly basis, private experiments on the assembly of the present invention have resulted in over nine months of continuous operation without leakage or breakage of the quartz chimney or injector tube.

Structurally, the present invention comprises a modified quartz element having plasma and auxiliary gas ports, a upper chimney mount, a unique chimney holder and injection tube mount, and a compression plug. The chimney holder and injection tube mount includes a specially machined groove so that a unique, double O-ring seal between the mount and the quartz element may be developed. This groove and double O-ring seal are advantageous over the prior art in that they allow for expansion and contraction of the quartz element without loss of seal integrity or breakage.

Additionally, the mount includes a specially designed bore for receiving two O-rings so that the injector tube is supported in and sealed with the mount only through the use of resilient O-rings. This arrangement is advantageous over the prior art in that it provides a more reliable seal while at the same time inhibiting injector tube breakage.

Other advantages include the use of a specially designed compression plug for applying uniform pressure to all sealing O-rings and for supporting the quartz element, and the use of a specially designed mount for restraining the double O-ring seal and for mounting the assembly to an ICP system. Other advantages will be made apparent to one skilled in the art upon review of this disclosure.

3. BRIEF DESCRIPTION OF THE DRAWINGS

FIGS. 3A-I, 3A-II and 3B illustrate a prior art Type II assembly and injector tube.

FIG. 4 illustrates the torch assembly of the present invention.

FIG. 5 illustrates the plasma and auxiliary gas connections for the present invention.

FIGS. 6A, 6B-I, 6B-II, 6C, 6D-I, 6D-II, 6D-III and 6D-IV illustrate the upper chimney mount of the present invention.

FIGS. 7A, 7B, 7C and 7D illustrate the chimney holder and injection tube mount of the present invention.

FIGS. 8A, 8B and 8C illustrates the compression plug of the present invention.

Figure 9:
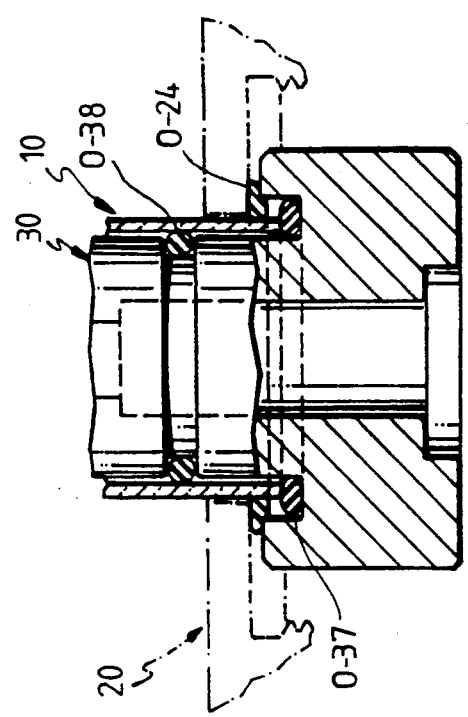
Figure 9:
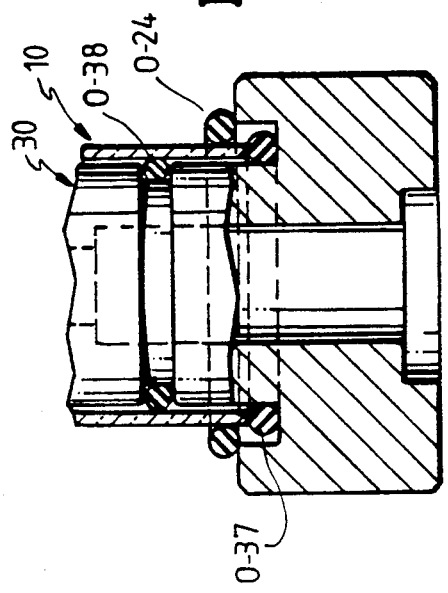
Figure 9:
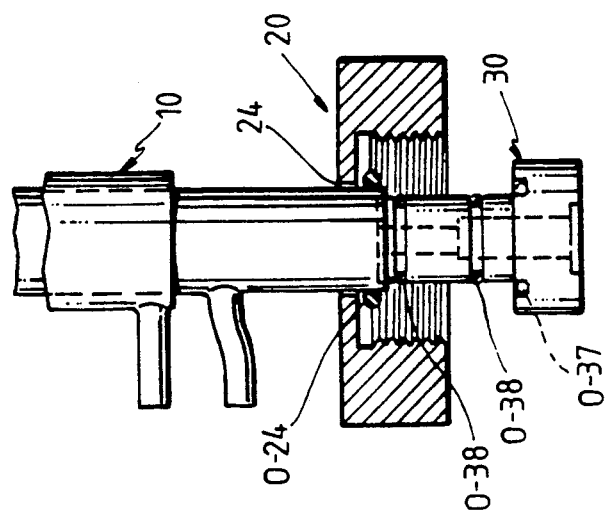

FIGS. 9A, 9B and 9C illustrate the seal between the quartz element and the chimney holder and injection tube mount of the present invention.

FIGS. 10A, 10B and 10C illustrate the seal between the chimney holder and injection tube mount and the injector tube of the present invention.

4. DESCRIPTION OF THE PREFERRED EMBODIMENT

As illustrated in FIG. 4 the complete torch support assembly of the present invention comprises a quartz chimney element 10, an upper chimney mount 20, a chimney holder and injection tube mount 30, and a compression plug 40.

4.1 The Quartz Chimney Element

The quartz element 10 of FIGS. 4 and 5 is a modified version of the quartz element used in prior art Type II assemblies. It has an inner chimney 11, an outer chimney 12, and ports 13 for plasma and auxiliary gas. Because the plasma and auxiliary gas ports are blown in quartz element 10, the need for an O-ring assembly to connect the plasma and gas ports (as in the Type I assemblies) is eliminated and fewer segmented parts are required.

The basic difference between the modified quartz element of the present invention 10 and prior art chimneys is the length of the base of the chimney. Because of the unique mount used in the present invention, it is often necessary to cut off a portion of the chimney base.

The exact length of the segment that must be cut off will depend on the size of the support assembly and can easily be determined by one skilled in the art. This modification may be accomplished through the use of well-known cutting methods. Additionally, it has been found advantageous to fire polish the base of the chimney after the cut is made. Satisfactory results have been obtained by modifying quartz tube, PE. No. 058-0528, manufactured by Perkin-Elmer.

In use, the ports 13 of the quartz element 10 are attached to sources of plasma and auxiliary gas (not shown) through tubing elements 14. This arrangement is illustrated in FIG. 5. Once the support assembly of the present invention is put together, little adjustment of the quarts element 10 is necessary. It has been found desirable, however, to reseat the plasma and auxiliary gas tubing elements 14 approximately every month. This reseating is necessitated by heat and ultraviolet light degradation to the tubing. Reseating of the tubing elements 14 does not require disassembly of the support apparatus and can be readily accomplished without the exertion of much time or effort. Alternate embodiments are envisioned where a shielding element is used to reduce the amount UV radiation and heat that reaches the tubing elements 14. Still further embodiments are envisioned where the tubing elements 14 comprise materials essentially resistant to heat or UV radiation.

4.2 The Upper Chimney Mount

One embodiment of the upper chimney mount for the present invention is illustrated in FIGS. 6A, 6B-I, 6B-II, 6C, 6D-I, 6D-II, 6D-III and 6D-IV. In this embodiment the upper chimney mount 20 comprises a single element 21 having a bore therethrough 22. Element 21 should be made of a material which will not significantly degrade when subject to the heat and radiation of an ICP torch. Examples of possible materials for element 21 are TEFLON, a tetrafluorethylene fluorocarbon polymer manufactured by duPont de Nemours & Co., Inc., and polyproplyne, although other materials may be used. In one embodiment, the top portion of element 21 is white (to reflect UV radiation) and the bottom portion is black.

Bore 22 has a first portion 23 and a second portion 24, with the first portion 23 having a cross-sectional area greater than that of the second portion 24. The first portion 23 of bore 21 preferably has some mechanism for receiving the compression plug 40. For example, in the embodiment of FIG. 6A the first portion 23 of bore 22 is threaded to receive a threaded compression plug. Alternate embodiments are envisioned where in other means (e.g., slots, half-threads, and the like) are utilized to receive the compression plug 40. The cross-sectional area of the second portion 24 of bore 22 is preferably slightly greater than the diameter of the base of quartz element 10.

The overall shape and configuration of upper chimney mount 21 is preferably designed to function as a mount to support and attach the assembly of the present invention to the ICP (not shown) and to allow the connection of the injector tube to the ICP mixing chamber (not shown). The precise configuration of element 21 will depend on the ICP system used, and can be determined by one skilled in the art.

An alternate embodiment of the upper chimney mount 20 is illustrated in FIGS. 6C and 6D. This embodiment is particularly designed for use when the support assembly of the present invention is used with in an existing Type II torch system.

In this alternate embodiment, the upper chimney mount 20 comprises a restraining cover 25, and a lower torch mount 26. The restraining cover 25 may be made of the same material discussed above for element 21. The cover 25, has a bore 22' therethrough that is preferable of diameter slightly larger than the diameter of quartz element 10. Holes (or slots) 27 are also provided; these holes may be threaded to receive a connecting screw. Extending from the bottom of restraining cover 25 is lip 28. This lip preferable extends only slightly from cover 25.

Lower torch mount 26 is preferably designed to enable the torch assemble to be mounted in the ICP system. One element that can function as the lower torch mount is the mount, PE. No. N058-1797, manufactured by Perkin-Elmer. For Type I ICP systems, the lower chimney mount is preferable circular in shape. A bore 29, extends through lower mount 26. The inner diameter of bore 29 should be only slightly larger than the outer diameter of lip 28 such that when the restraining cover and lower mount are fitted together, lip 28 inhibits axial movement. Lower mount 26 include holes 27' arranged to correspond to holes 27. When the upper and lower mounts are fitted together, fasting means (e.g., screws, nuts and bolts, and the like) may be passed through holes 27 and 27' to securely affix the lower mount 26 to the restraining cover 25.

A connecting portion 24' extends from the bottom of lower mount 26. This portion 24' is preferably designed to receive a compression plug in a manner similar to that discussed above in regard to portion 24.

4.3 The Chimney Holder and Injection Tube Mount

FIGS. 7A-7D illustrate the chimney holder and injection tube mount 30 of the present invention. The mount 30 is preferably made of TEFLON, a tetrafluorethylene fluorocarbon polymer manufactured by duPont de Nemours & Co., Inc., PLEXIGLASS, a thermoplastic poly(methyl methacrylate)-type polymer available from Rohm & Haas Co., FE FLOW, or polypropylene although other suitable materials may be used.

Figure 2:
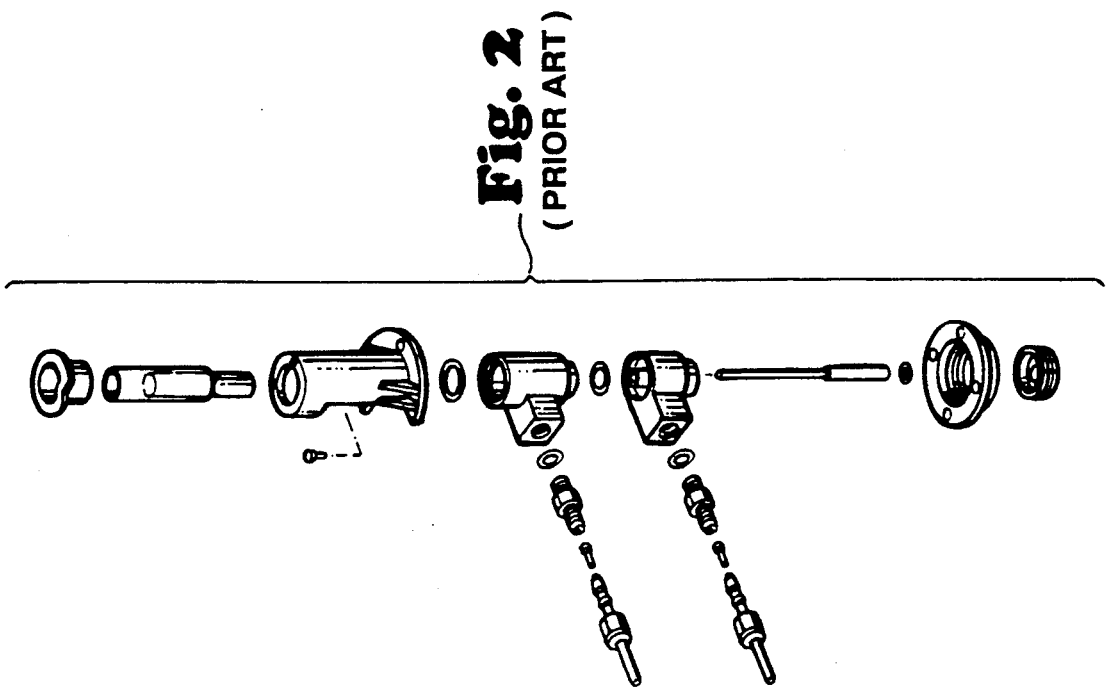
FIG. 2 illustrates a prior art Type I assembly.
Figure 1:
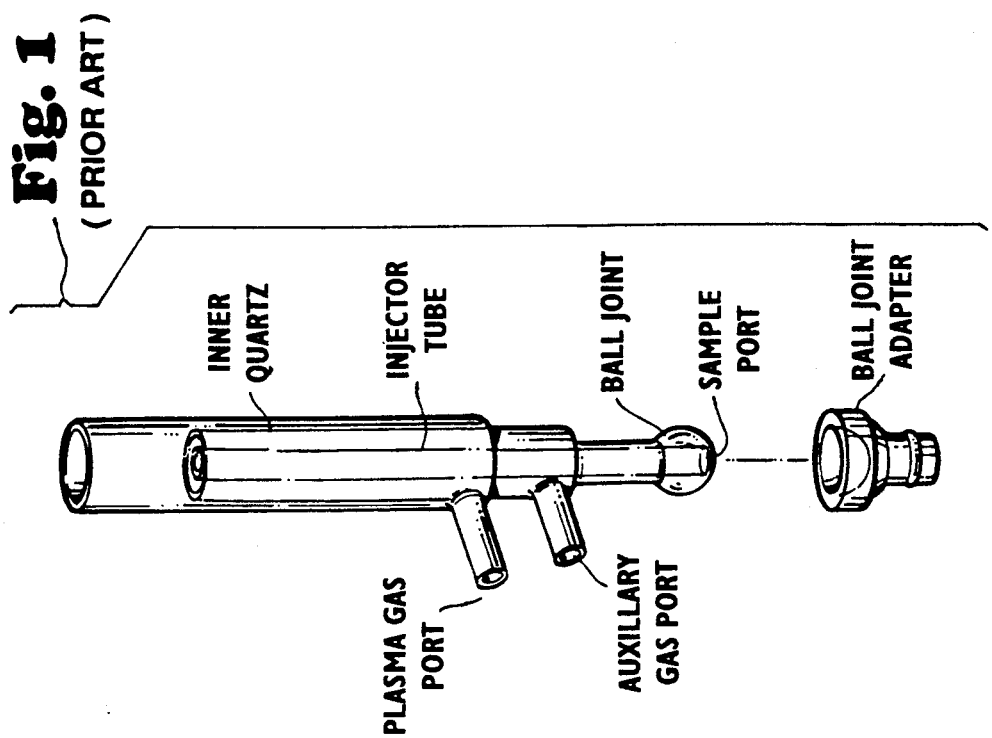
FIG. 1 illustrates a prior art Quartz assembly.
Figure 7:
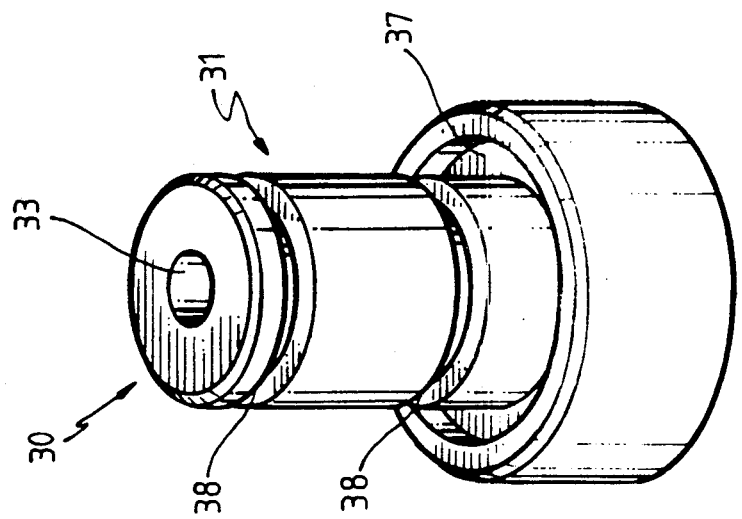
Figure 7:
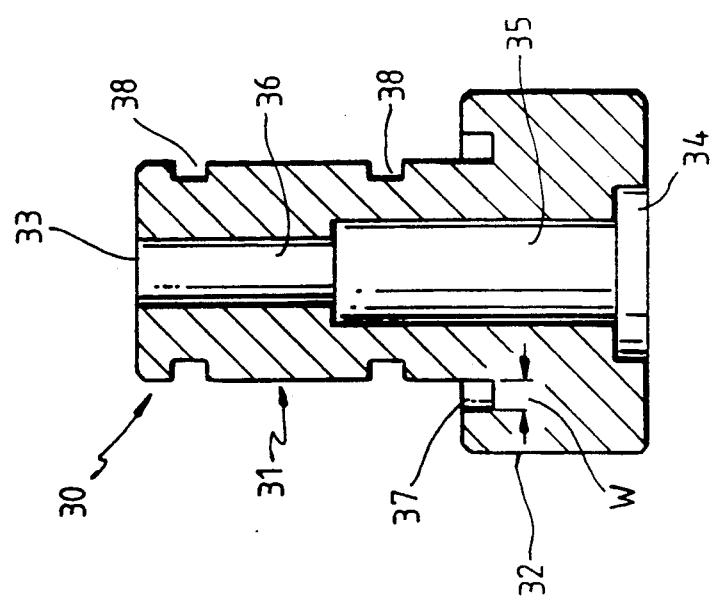

As illustrated in FIGS. 7A and 7B, mount 30 generally comprises a shaft 31 and a base 32. A bore 33 having a first portion 34, a second portion 35, and a third portion 36 passes through both the shaft 31 and the base 32 of mount 30. As illustrated in FIG. 7C, when assembled, shaft 31 supports quartz element 10 and base 32 effects a seal between the mount 30 and the base of quartz element 10.

The diameter of the shaft 31 is preferably slightly less than that of the inner diameter of the base of quartz element 10. Additionally, shaft 31 may include one or more annular groves 38 each capable of receiving a single O-ring O-38. When placed in groves 38, the O-rings O-38 provide a surface for supporting quartz element 10. In one embodiment two annular groves 38 are provided, each spaced approximately 0.4 inches from the other. Although O-rings made of VITON, a fluoroelastomer based on the copolymer of vinyliden fluoride and hexafluoropropylene manufactured by duPont de Nemours & Co., Inc., have been found particularly suitable for the present invention, O-rings O-38 may comprise any suitably compressible and resilient material.

While O-rings O-38 initially effect a seal of quartz element 10, they are expected to suffer UV and heat degradation. As such, the integrity of the seal in the present invention for quartz element 10 does not rest on these O-rings. The mechanism for effecting this seal in the present invention is discussed in Section 4.5.1, below.

An a single O-ring groove 37, is machined into base 32 at the lower end of shaft 31. The inner radius of groove 37 should be the same as that of the outer radius of shaft 31, i.e., it should be less than the inner radius of the base of quartz element 10. The outer radius of groove 37 should be such that the width of the groove W is greater than the distance between the inner and outer diameters of the base of quartz element 10.

When the support assembly of the present invention is put together, groove 37 receives an O-ring O-37. This O-ring is preferably made of a material that is more resilient that used for O-rings O-35 although the precise composition of these O-rings is not essential. O-rings made of soft rubber have been found suitable. The inner diameter of O-ring O-37 should be such that it can fit over the shaft 31 and into groove 37. When there is no pressure on O-ring O-37, its outer diameter should be less than the outer diameter of groove 37. Additionally, the width of O-ring O-37 should be greater than the distance between the inner and outer diameters of the base of quartz element 10. In one preferred embodiment, the width of O-ring 37 is between 1.33 and 2 times the distance between the inner and outer diameters of the base of quartz element 10. When the support assembly of the present invention is in use, O-ring 37 effects a seal on quartz element 10. This seal is discussed in Section 4.5.2, below.

As noted above, bore 33 has three portions having different diameters: 34, 35, and 36. The diameter of these portions are selected so that bore 33 can accommodate a Type I alumina injector tube (FIG. 7D). As illustrated, the Type I injector consists of two parts—a first part, and a second part having a diameter smaller than that of the first part. Such Type I injector tubes are commercially available and alumina injector tubes, PE Nos. 0047-3500, and 058-1616, manufactured by Perkin-Elmer have been found particularly suited for use with the present invention.

The total length of bore 33 should be such that it can accommodate both the large diameter portion of a Type I injector tube and the portion having the smaller diameter. In particular, portion 36 of bore 33 should be machined so that it can accommodate the smaller diameter of a Type I injector tube; additionally, portion 35 of bore 33 should be machined to accommodate the larger diameter of such an injector tube. Portion 34 of bore 34, should have an outer diameter larger than that for portions 35 and 36 and should be capable of accommodating a large O-ring. When in use, bore 33, in combination with several O-rings effectively seals the injector tube. The injector tube seal for the present invention is discussed in Section 4.5.2, below.

4.4 The Compression Plug

FIG. 8 illustrates the compression plug 40 of the present invention. As illustrated, the compression plug comprises a first portion 41 and a second portion 42 with a bore 43 passing through the entire plug. The outer surface of the first portion 41 is preferable adapted to be received into the receiving portion 24 of the upper chimney mount 20. In the illustrated embodiment, portion 41 is threaded so as to be screwably mountable in portion 24 of mount 20.

The second portion 42 of plug 40 is preferably provided with a means for securely fitting the plug tightly into the upper chimney mount. In the illustrated embodiment, portion the outer portion 42 consists of a knurled edge such that plug 40 may be screwed by hand into the upper chimney mount. In this embodiment, no tools are required to complete the support assembly and the construction approach is relatively simple. Alternate embodiments are envisioned wherein the second portion 42 included recesses for receiving a special tool for inserting the plug 40 into the upper chimney mount.

The bore 43 passing through the plug preferably has two regions each having a different diameter. The inner diameter of the larger regions should be slightly larger than the outer diameter of the base 32 of mount 30, and the inner diameter of the smaller region should be slightly larger than the largest outer diameter of the injector tube.

Plug 40 may comprise the same material as the upper chimney mount.

4.5 The Seals

In the present invention, there are only three locations where leakage may occur: (1) at the seal at the plasma and auxiliary gas ports 13, (2) at the seal between the quartz element 10 and mount 30, and (3) at the seal between the injector tube and mount 30. As discussed above, the integrity of the seal at the plasma and gas ports is maintained by reseating the tubing approximately every month. Thus, the following sections are directed primarily towards the seal between the quartz element 10 and the mount 30 and the seal between the injector tube and mount 30.

4.5.1 The Seal Between the Quartz Element and the Mount

FIGS. 9A-9C illustrate the seal between the quartz element 10 and the mount 30 for the present invention. As noted above, in the present invention, O-rings O-38 provide support—not sealing. In the device of the present invention, sealing of quartz element 10 occurs in the region of groove 37, substantially at the base of element 10. This location for the seal is advantageous in that is located distal from the plasma and thus is not subject to significant heat and UV degradation.

The basic mechanisms for sealing quartz element 10 in the present invention are illustrated in FIGS. 9A and B. FIGS. 9A and B illustrate the apparatus of the present invention before any pressure is applied by the compression plug 40, i.e., before compression plug 40 is inserted (or tightened) into upper chimney mount 20. As illustrated in FIG. 9A, during assembly, the base of quartz element 10 is passed through the smaller portion of bore 24. An O-ring, O-24, is then placed on the outside of the base of quartz element 10. O-ring O-24 is preferably made of the same material as O-ring O-37, e.g., soft rubber. The outer diameter of O-ring O-24 should be such that, when mount 30 is brought into contact with element 10, it overlaps groove 37 by approximately 40-50 percent. A close-up of the relationship between the mount 30, quartz element 10, and O-rings O-24 and O-37 is illustrated in FIG. 9B.

When a uniform source of pressure is brought to bear on the upper surface of O-ring O-24, e.g., when the compression plug 40 is inserted into the upper chimney mount 20 and tightened, a portion of O-ring O-24 is distorted downward into groove 37. Surface tension on the inner radius of O-ring 24 is expressed upon the base of quartz element 10, forcing the base of element 10 downward on O-ring O-37 causing O-ring O-37 to distort. When the resilience of O-ring O-37 equals that of the surface tension force directed downward an equilibrium seal develops. This equilibrium seal allows changes with heat induced expansion and remains in effect as long as O-ring O-24 is forced into groove 37 with sufficient tension to force quartz element 10 downward. A close-up of this seal is illustrated in FIG. 9C.

A unique advantage of the seal illustrated is FIG. 9C is that it allows for heat expansion and contraction of quartz element 10 and mount 20 without destroying the integrity of the seal or breaking element 10. As illustrated, even when the initial seal is developed, O-ring O-37 does not completely fill groove 37. Thus, if element 10 begins to expand lengthwise due to heat from the plasma torch, there is room for O-ring expansion. Further, because there is still room for O-ring O-24 to distort into groove 37, element 10 can expand cross wise. This unique double O-ring seal also allows for the contraction of element 10 without destruction of seal integrity.

Another advantage of the double O-ring seal of the present invention is that it is located distal from the plasma and thus is not subject to rapid UV and heat degradation. Additionally, because the shaft 31 of base 30 is used to support element 10, coaxial containment of element 10 is not required on exterior surfaces in close proximity to the plasma. The absence of these exterior parts allows for better transfer of heat trapped in the chimney into the surrounding air. The result of this is reduced chimney breakage and inhibition of leaks at the plasma and auxiliary gas ports. Accompanying the reduced leakage is reduced sample plugging of the injector tube which allows uninterrupted operation of the ICP instrument.

A still further advantage of the double O-ring seal is that it results from the interaction of two, easily manufacturable O-rings. As such, precise machining with small tolerances of mount 20 is not required. Thus the use of O-rings and groove 37 for heat expansion eliminates precise lathe work for seal development.

4.5.2 The Seal Between the Injector Tube and the Mount

In addition to essentially eliminating leaks at the nexus of element 10 and mount 20, the device of the present invention essentially eliminates leaks at the seal between the injector tube and mount 30. This seal is illustrated in FIGS. 10A-10C.

In contrast to prior art devices, in the present invention the injector tube is totally suspended, sealed and secured in a mount through the use of two O-rings and the same uniform pressure source utilized for sealing the quartz element against the mount.

FIG. 10A illustrates the apparatus of the present invention before any pressure is applied, e.g., before the compression plug 40 is inserted onto the upper mount 20 and tightened. As illustrated, two O-rings, O-35 and O-34 are placed on the injector tube. O-ring O-35 is placed over the small tubing of the injector tube and O-ring O-34 is placed over the large diameter of the tube. As with O-rings 38, O-rings O-34 and O-35 may be made of VITON, a fluroelastomer based on the copolymer of vinyliden fluoride and hexafluoropropylene manufactured by duPont de Nemours & Co., Inc..

O-ring O-35 and bore 33 are preferably sized such that O-ring O-35 must be forced into portion 35 of bore 33 before the top of the large diameter portion of the injector tube enters bore 33. In one embodiment, O-ring O-35 and bore 33 are sized such that the outer diameter of O-35 is 5-10% larger than the inner diameter of portion 35 of bore 33. Thus, when the assembly of the present invention is configured, O-ring O-35 is placed on the smaller portion of the injector tube, the injector tube may then be forced, by hand, into mount 30 such that the smaller diameter tubing of the injector tube, along with O-35 are positioned in portion 35 of bore 33. FIG. 10B illustrates mount 20 with the first portion of the injector tube inserted therein.

Note that only the side walls of portion 35 of bore 33 are used to effect this seal—it is not necessary that O-ring O-35 be forced against and extending lip of the bore. The result of this unique seal is that the height of the injector tube may be variably adjusted without destroying the integrity of the seal. Additionally, this unique design eliminates the stress breakage found in prior art devices induced when the injector tube is forced against non-resilient surfaces.

In addition to O-ring O-35, a larger O-ring, O-34 is also used to effect the seal between the injector tube and the mount 30. This O-ring is placed over the larger diameter tubing of the injector tube and is preferable designed to fit on the portion 34 of groove 33. Additionally, the outer diameter of O-ring O-34 should be such that it is greater than the diameter of the bottom hole for compression plug 40. Thus, once the smaller tubing of the injector tube is inserted into bore 33, uniform pressure (from compression plug 40) can be applied to O-ring O-34 such that a seal is effected between the mount 30, O-ring)-34 and the injector tube. This seal provides a backup in the event the seal created by O-ring O-35 should somehow fail. An additional advantage of using two O-rings is that the injector tube is supported and sealed only be resilient materials. As such, there is some room for expansion or contraction of the injector tube without the risk of breakage. The complete seal for the injector tube is illustrated in FIG. 10C.

When determining the size of injector tube to use with the present invention, sufficient length of the large diameter section of the tube should be allowed for connection with the ICP mixing chamber (not shown).

4.6 Alternate Embodiments

Alternate embodiments of the present invention are envisioned wherein Type II injector tubes (i.e., injector tubes not having portions of large and small diameters, refer to FIG. 3B) are used. In these embodiments the bore 33 in mount 30 is modified to accommodate the different shape of the injector tube. All other features of the present device should remain essentially the same.

I claim as my invention:

1. A torch support assembly comprising:
   (a) a torch element having a bore passing therethrough and a base;
   (b) an upper chimney mount having a bore therethrough, the base of the torch element passing through the bore of the chimney mount;
   (c) an injection tube mount having a shaft and a base, the base of the injection tube mount having an annular groove located at the base-end of the shaft, the injection tube mount positioned such that the shaft fits within the base of the torch element;
   (d) a first O-ring positioned in the groove located at the base-end of the shaft, a second O-ring positioned around the base of the torch element, the outer diameter of the second O-ring being larger than the outer diameter of the groove, the two O-rings operating to effect a seal between the injection tube mount and the base of the torch element; and (e) a compression plug for applying uniform pressure to the first and second O-rings.

2. The torch support assembly of claim 1 wherein the torch element comprises blown quartz.

3. The torch support assembly of claim 2 wherein the quartz torch element has ports for plasma and auxiliary gas and the assembly is positioned in an inductively coupled plasma spectrometer.

4. The torch support assembly of claim 1 wherein the bore in the upper chimney mount defines a first portion and a second portion, the first portion having a cross-sectional area greater than that of the second portion.

5. The torch support assembly of claim 4 wherein the first portion of the bore in the upper chimney mount includes means for receiving the compression plug.

6. The torch support assembly of claim 5 wherein the compression plug is threaded and the bore in the upper chimney mount is threaded to receive the compression plug.

7. The torch support assembly of claim 1 wherein the upper chimney mount is designed to serve as a mount to support the torch support assembly in an inductively coupled plasma spectrometer.

8. The torch support assembly of claim 1 wherein the upper chimney mount comprises a restraining cover and a lower torch mount.

9. The torch support assembly of claim 8 wherein the restraining cover includes a downwardly extending lip and the lower torch mount includes a bore slightly larger than the lip, such that the lip fits in the bore of the lower torch mount.

10. The torch support assembly of claim 8 wherein both the restraining cover and the lower torch mount have a hole passing therethrough and a fasting device is positioned in the hole to fasten the restraining cover to the lower torch mount.

11. The torch support assembly of claim 1 wherein the injection tube mount is made of plexiglass.

12. The torch support assembly of claim 1 wherein the shaft includes a second annular groove, and a third O-ring is positioned in the second annular groove so as to provide a surface for supporting the torch element.

13. The torch support assembly of claim 1 wherein the inner radius of the annular groove located at the base-end of the shaft is less than the inner radius of the base of the torch element and the outer radius of the groove is such that the width of the groove is greater than the distance between the inner and outer diameters of the base of the torch element.

14. The torch support assembly of claim 1 wherein the width of the first O-ring is such that, when uncompressed, its outer diameter is less than the outer diameter of the groove located at the base-end of the shaft.

15. The torch support assembly of claim 1 wherein the uncompressed width of the first O-ring is between 1.33 and 2 times the distance between the inner and outer diameters of the base of the torch element.

16. The torch support assembly of claim 1 wherein there is a bore passing through the compression plug, the bore defining a first portion and a second portion, the outer surface of the first portion adapted to be received by the upper chimney mount and the second portion including means for forcing the plug into the upper chimney mount.

17. The torch support assembly of claim 16 wherein both the plug and the bore in the upper chimney mount are threaded and the means for forcing the plug into the upper chimney mount comprise a knurled surface such that the plug may be screwed into the upper chimney mount by hand.

18. A support assembly for an injector tube having a large diameter tube region and a small diameter tube region comprising:
(a) a torch element having a bore passing therethrough and a base;
(b) an upper chimney mount having a bore therethrough, the base of the torch element passing through the bore of the chimney mount;
(c) an injection tube mount having a shaft, a base, and a bore passing through both the shaft and the base of the mount, the bore defining a first portion, a second portion, and a third portion, the inner diameter of the first portion being greater than the inner diameter of the second portion, and the inner diameter of the second portion being greater than the inner diameter of the third portion;
(d) a first O-ring positioned around the large diameter region of the injector tube, the first O-ring located within the first portion of the mount bore;
(e) a second O-ring positioned around the small diameter tube region of the injector, the second O-ring located within the second portion of the mount bore; and
(f) a compression plug for applying uniform pressure to the first and second O-rings.

19. The support assembly of claim 18 wherein the uncompressed outer diameter of the second O-ring is greater than the inner diameter of the second portion of the mount bore.

20. The support assembly of claim 19 wherein the uncompressed outer diameter of the second O-ring in 5–10% larger than the inner diameter of the second portion of the mount bore.

21. A torch support assembly for an injector tube having a large diameter tube region and a small diameter tube region comprising:
(a) a torch element having a bore passing therethrough and a base;
(b) an upper chimney mount having a bore therethrough, the base of the torch element passing through the bore of the chimney mount;
(c) an injection tube mount having a shaft, a base, and a bore passing through both the shaft and the base of the mount, the bore defining a first portion, a second portion, and a third portion, the inner diameter of the first portion being greater than the inner diameter of the second portion, and the inner diameter of the second portion being greater than the inner diameter of the third portion, the mount base having an annular groove located at the base-end of the shaft, the mount positioned such that the shaft fits within the base of the torch element;
(d) a first O-ring positioned around the large diameter region of the injector tube, the first O-ring being located within the first portion of the mount bore;
(e) a second O-ring positioned around the small diameter tube region of the injector, the second O-ring being located within the second portion of the mount bore;
(f) a third O-ring positioned in the groove located at the base-end of the shaft, a fourth O-ring positioned around the base of the torch element, the outer diameter of the fourth O-ring being larger than the outer diameter of the groove; and
(g) a compression plug for applying uniform pressure to the first, second, third, and fourth O-rings.

22. The torch support assembly of claim 21 wherein the uncompressed outer diameter of the second O-ring is greater than the inner diameter of the second portion of the mount bore.

23. The torch support assembly of claim 22 wherein the uncompressed outer diameter of the second O-ring in 5-10% larger than the inner diameter of the second portion of the mount bore.

24. The torch support assembly of claim 21 wherein the bore in the upper chimney mount defines a first chimney mount portion and a second chimney mount portion, the first chimney mount portion having a cross-sectional area greater than that of the second chimney mount portion.

25. The torch support assembly of claim 24 wherein the first chimney mount portion includes means for receiving the compression plug.

26. The torch support assembly of claim 21 wherein the shaft includes a second annular groove, and a fifth O-ring is positioned in the second annular groove so as to provide a surface for supporting the torch element.

27. The torch support assembly of claim 21 wherein the inner radius of the annular groove located at the base-end of the shaft is less than the inner radius of the base of the torch element and the outer radius of the groove is such that the width of the groove is greater than the distance between the inner and outer diameters of the base of the torch element.

28. The torch support assembly of claim 21 wherein the width of the third O-ring is such that, when uncompressed, its outer diameter is less than the outer diameter of the groove located at the base-end of the shaft.

29. The torch support assembly of claim 21 wherein the uncompressed width of the third O-ring is between 1.33 and 2 times the distance between the inner and outer diameters of the base of the torch element.

30. An assembly for supporting and sealing an plasma torch tube having a large diameter tube region and a small diameter tube region and for sealing a chimney element, the assembly comprising:
(a) a chimney element having a bore passing therethrough and a base;
(b) an upper chimney mount for supporting the chimney element, the upper chimney mount having a bore passing therethrough, the base of the chimney element passing through the bore of the upper chimney mount;
(c) an injection tube mount for supporting an injection tube, the injection tube mount having a shaft, a base, and a bore passing through both the shaft and the base, the bore defining a first portion, a second portion, and a third portion, the inner diameter of the first portion being greater than the inner diameter of the second portion, and the inner diameter of the second portion being greater than the inner diameter of the third portion, the base having an annular groove located at the base-end of the shaft, the injection tube mount positioned such that the shaft fits within the base of the chimney element and supports the chimney element;
(d) a first O-ring positioned around the large diameter region of the injector tube, the first O-ring located within the first portion of the mount bore to effect a seal between the large diameter region of the injector tube and the first portion of the injector tube mount bore;
(e) a second O-ring positioned around the small diameter tube region of the injector tube, the second O-ring being located within the second portion of the injection tube mount bore to effect a seal between the small diameter region of the injector tube and the second portion of the injector tube mount bore;
(f) a third O-ring and a fourth O-ring, the third O-ring positioned in the groove located at the base-end of the shaft and the fourth O-ring positioned around the base of the chimney element, the outer diameter of the fourth O-ring being larger than the outer diameter of the groove, the combination of the third and fourth O-rings effecting a seal between the chimney element and the injection tube mount; and
(g) a compression plug affixed to the upper chimney mount for applying uniform pressure to the first, second, third, and fourth O-rings.

31. An sealing assembly for effecting a seal with a fragile element, the fragile element having a bore passing therethrough, the assembly comprising:
(a) a mount having a shaft and a base, the base having an annular groove located at the base-end of the shaft, the shaft sized such that it fits within the bore passing through the fragile element;
(b) a first O-ring and a second O-ring, the first O-ring positioned in the groove located at the base-end of the shaft and the second O-ring positioned around the fragile element, the outer diameter of the second O-ring being larger than the outer diameter of the groove, the combination of the first and second O-rings effecting a seal between the fragile element and the mount; and
(c) compression means for applying pressure to the first and second O-rings.

* * * * *

UNITED STATES PATENT AND TRADEMARK OFFICE
CERTIFICATE OF CORRECTION

PATENT NO. : 5,186,621

DATED : March 30, 1993

INVENTOR(S) : H. DALE PENNINGTON

It is certified that error appears in the above-identified patent and that said Letters Patent is hereby corrected as shown below:

In claim 30, col. 15, line 38, after "torch" insert --injector--.

Signed and Sealed this

Sixteenth Day of November, 1993

Attest:

BRUCE LEHMAN

*Attesting Officer*  Commissioner of Patents and Trademarks